United States Patent [19]

Hyer et al.

[11] 4,254,055

[45] Mar. 3, 1981

[54] SYNTHESIS OF TETRASODIUM PENTAERYTHRITYL TETRAKIS (DITHIOCARBAMATE)

[75] Inventors: Harry J. Hyer, Los Gatos; John E. Sundberg, Fairfax, both of Calif.

[73] Assignee: United Technologies Corporation, Hartford, Conn.

[21] Appl. No.: 803,840

[22] Filed: Jun. 6, 1977

[51] Int. Cl.$^3$ .......................................... C07C 155/00
[52] U.S. Cl. .................................................. 260/513.5
[58] Field of Search ..................................... 260/513.5

[56] References Cited

U.S. PATENT DOCUMENTS 2,609,389  9/1952  Flenner ............................ 260/513.5

Primary Examiner—Nicky Chan
Attorney, Agent, or Firm—Steven F. Stone

[57] ABSTRACT

Tetrasodium pentaerythrityl tetrakis (dithiocarbamate) has been found to be an unusually stable lead precipitant which can be incorporated in coatings to be applied over lead painted surfaces to detoxify the same. The preparation of TSPTD from carbon disulfide sodium hydroxide and pentaerythrityl tetramine by simple mixing thereof does not produce satisfactory yields because of undesirable side reactions. The TSPTD can be produced in high yields by the gradual addition of sodium hydroxide to a mixture of pentaerythrityl tetramine in an excess of carbon disulfide.

4 Claims, No Drawings

SYNTHESIS OF TETRASODIUM PENTAERYTHRITYL TETRAKIS (DITHIOCARBAMATE)

GOVERNMENT RIGHTS

The Government has rights in this invention pursuant to Contract Number H-2284R, awarded by the Department of Housing and Urban Development.

BACKGROUND OF THE INVENTION

TSPTD has been found to be a excellent lead precipitant for use in the detoxification of lead paint covered surfaces. The conventional method of manufacturing TSPTD from carbon disulfide sodium hydroxide and pentaerythrityl tetramine produces poor yields as a result of undesirable side reactions. According to this invention we have discovered a method for manufacturing TSPTD from carbon disulfide, sodium hydroxide and pentaerythrityl tetramine which produces yields in the order of 78% of theoretical. It is accordingly an object of this invention to provide a method of synthesis of TSPTD. These and other objects of the invention will be readily apparent from the following description of the invention.

DESCRIPTION OF THE INVENTION

The method of making TSPTD from pentaerythrityl tetramine, carbon disulfide sodium hydroxide proceeds according to the following reaction:

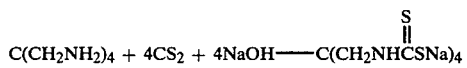

Owing to yield reducing side reactions, simple mixing of the tetramine with four equivalents of carbon disulfide and sodium hydroxide does not produce a satisfactory yield. According to this invention it has been found that substantially greater yields can be obtained if the reaction is carried out in the presence of a slightly basic, water soluble, inert solvent such as pyridine in the presence of an excess of carbon disulfide with the sequential addition of sodium hydroxide. The following example illustrates this invention, however, it should be recognized that while the example relates specifically to sodium hydroxide and the preparation of the sodium salt it is usable in connection with any of the alkali metal salts.

EXAMPLE I

Preparation of Tetrasodium Pentaerythrityl Tetrakis (Dithiocarbamate)

16.1 grams (0.212 mols) of carbon disulfide and five milliliters of pyridine were placed in a 100 milliliter three-necked Morton flask equipped with a mechanical stirrer, reflux condenser and two addition funnels. Three drops of 1% phenolphthalein were added and the reaction flask was placed in an ice bath. The mixture was cooled to below about 5° C. and 3.5 grams (0.0265 mols) of distilled pentaerythrityl tetramine dissolved in 7 milliliters of pyridine were slowly added with vigorous stirring. A precipitate formed immediately. The reaction flask was removed from the ice bath and three molar aqueous sodium hydroxide was slowly added until the pink color appeared. After a reaction period of several minutes, the pink color disappeared; sodium hydroxide solution was again added with continuous vigorous stirring until the pink color reappeared. This process was repeated until a total 34.5 milliliters (0.106 mols) of sodium hydroxide solution was added. At this point the orange reaction mixture contained two liquid layers and no solid material. The reaction mixture was then evaporated to dryness on a vacuum rotary evaporator and the solid residue recrystalized from ethanol to give 14.0 grams of colorless crystals. The NMR of the recrystalized material indicated its composition to be

The 14 grams thus corresponds to a yield of 78% of the theoretical.

While this invention has been described with respect to a specific embodiment thereof it should not be construed as being limited thereto. Modification can be made by workers skilled in the art without departing from the scope of the invention which is limited only by the following claims wherein:

We claim:

1. A method for manufacturing the alkali metal salt of pentaerythrityl tetrakis dithiocarbamate from carbon disulfide, pentaerythrityl tetramine and alkali metal hydroxide which comprises:
   (a) placing in a reaction vessel carbon disulfide and a slightly basic, water soluble inert solvent therefor;
   (b) cooling said mixture to below about 5° C.;
   (c) adding pentaerythrityl tetramine to the cooled carbon disulfide with stirring;
   (d) stopping cooling of said reaction mixture after a precipitate has formed;
   (e) adding an aqueous solution of alkali metal hydroxide to said reaction mixture slowly until a basic condition is obtained;
   (f) permitting the reaction to continue until an acidic condition is obtained;
   (g) adding additional alkalai metal hydroxide and repeating steps (e) and (f) until sufficient alkalai metal hydroxide has been added to complete the conversion at which time a mixture containing two liquid layers and no solid will be obtained; and
   (h) evaporating said reaction mixture to dryness.

2. The method of claim 1 wherein said solvent is pyridine.

3. The method of claim 1 wherein said alkali metal is sodium.

4. The method of claim 3 where said solvent is pyridine.